United States Patent
Bergonzelli Degonda et al.

(10) Patent No.: US 9,662,358 B2
(45) Date of Patent: May 30, 2017

(54) COMPOSITION FOR USE IN THE PROMOTION OF HEALTHY BONE GROWTH AND/OR IN THE TREATMENT OF BONE DISEASE

(71) Applicant: NESTEC S.A., Vevey (CH)

(72) Inventors: Gabriela Bergonzelli Degonda, Bussigny (CH); Euridice Castaneda Gutierrez, Pully (CH); Clara Garcia-Rodenas, Forel (CH); Elizabeth Offord Cavin, Montreux (CH); Stephanie Viguet-Carrin, Epalinges (CH)

(73) Assignee: Nestec S.A., Vevey (CH)

( * ) Notice: Subject to any disclaimer, the term of this patent is extended or adjusted under 35 U.S.C. 154(b) by 178 days.

(21) Appl. No.: 14/352,590

(22) PCT Filed: Oct. 15, 2012

(86) PCT No.: PCT/EP2012/070370
§ 371 (c)(1),
(2) Date: Apr. 17, 2014

(87) PCT Pub. No.: WO2013/057063
PCT Pub. Date: Apr. 25, 2013

(65) Prior Publication Data
US 2014/0248247 A1  Sep. 4, 2014

(30) Foreign Application Priority Data
Oct. 18, 2011  (EP) .................... 11185608

(51) Int. Cl.
*A61K 35/747* (2015.01)
*A61K 35/741* (2015.01)
*A61K 31/202* (2006.01)
*A61K 31/702* (2006.01)
*A23L 33/12* (2016.01)
*A23L 33/135* (2016.01)
*A23L 33/21* (2016.01)
*A23L 33/00* (2016.01)

(52) U.S. Cl.
CPC ............ *A61K 35/747* (2013.01); *A23L 33/12* (2016.08); *A23L 33/135* (2016.08); *A23L 33/21* (2016.08); *A23L 33/40* (2016.08); *A61K 31/202* (2013.01); *A61K 31/702* (2013.01); *A61K 35/741* (2013.01); *A23V 2002/00* (2013.01)

(58) Field of Classification Search
None
See application file for complete search history.

(56) References Cited

U.S. PATENT DOCUMENTS

| 2007/0098821 | A1 | 5/2007 | Johnson |
| 2007/0154992 | A1* | 7/2007 | DeFrees ................. A61K 38/27 435/69.4 |
| 2009/0118229 | A1 | 5/2009 | Jouni et al. |
| 2010/0278781 | A1* | 11/2010 | Hougee ................. A23L 1/3014 424/93.4 |

FOREIGN PATENT DOCUMENTS

| WO | WO 00/44367 | * | 8/2000 | ............ A61K 31/00 |
| WO | 2006130205 | | 12/2006 | |
| WO | 2007101675 | | 9/2007 | |
| WO | 2008153377 | | 12/2008 | |
| WO | 2011060123 | | 5/2011 | |
| WO | WO 2012170021 A1 | * | 12/2012 | ........... A23C 9/1512 |

OTHER PUBLICATIONS

Marshall, D. et al. 1996. Meta-analysis of how well measures of bone mineral density predict occurrence of osteoporotic fractures. The BMJ 312: 1254-1271. specif. p. 1254, 1255.*
Zhang et al. "N-3 polyunsaturated fatty acids and bone metabolism" Chin. J. Osteoporos., vol. 17, No. 6, 2011, pp. 556-561.
Huang et al. "The role of immune factors in the development of osteoporosis" Chin. J. Osteoporos., vol. 16, No. 3, 2010, pp. 225-227.
International Search Report corresponding to related International Patent Application No. PCT/EP2012/070370 mailed Nov. 13, 2012.
International Written Opinion corresponding to related International Patent Application No. PCT/EP2012/070370 mailed Nov. 13, 2012.
Borelli F. et al., Alternative and Complementary Therapies for Menopause, Maturitas Aug. 2010 66(4), http://www.ncbi.nlm.nih.gov/pubmed/20580501, pp. 333-343 (Abstract).
Lukas R. et al., Consumption of Different Sources of Omega-3 Polyunsaturated Fatty Acids by Growing Females Rats Affects Long Bone Mass and Microarchitecture, Bone, 2011 (Sep;49(3), http://www.ncbi.nlm.nih.gov/pubmed/21672645, 2011, pp. 455-462 (Abstract).
Kruger et al. "Long-chain polyunsaturated fatty acids: Selected mechanisms of action on bone" Progress in Lipid Research, 2010, vol. 49, pp. 438-448.
Scholz-Ahrens et al. "Prebiotics, Probiotics, and Synbiotics Affect Mineral Absorption, Bone Mineral Content, and Bone Structure1-3" The Journal of Nutrition, 2007, vol. 137, pp. 838S-846S.

* cited by examiner

*Primary Examiner* — Renee Claytor
*Assistant Examiner* — Sharon M Papciak
(74) *Attorney, Agent, or Firm* — K&L Gates LLP (57) ABSTRACT

The invention discloses a composition comprising at least one long chain polyunsaturated fatty acid, at least one probiotic and a mixture of oligosaccharides, said mixture containing at least one N-acetylated oligosaccharide, at least one sialylated oligosaccharide and at least one neutral oligosaccharide, for use in the promotion of healthy bone growth and/or in the prevention and/or treatment of bone disease. Said bone disease is in particular osteomalacia, rickets, osteopenia or osteoporosis. Preferably the composition is a nutritional composition.

23 Claims, 1 Drawing Sheet

COMPOSITION FOR USE IN THE PROMOTION OF HEALTHY BONE GROWTH AND/OR IN THE TREATMENT OF BONE DISEASE

CROSS REFERENCE TO RELATED APPLICATIONS

The present application is a National Stage of International Application No. PCT/EP2012/070370, filed on Oct. 15, 2012, which claims priority to European Patent Application No. 11185608.4, filed Oct. 18, 2011, the entire contents of which are being incorporated herein by reference.

FIELD OF THE INVENTION

This invention relates to a composition for use in the prevention and/or treatment of bone disease, such as the promotion of healthy bone growth, and the prevention or treatment of osteopenia, osteomalacia or rickets, or osteoporosis. This composition is for use in mammals, preferably in humans.

BACKGROUND OF THE INVENTION

Osteopenia is a condition characterized by deficient organic bone matrix leading to amounts of bone tissue lower than normal.

Osteomalacia is a condition where bone mineral density (BMD) and bone mineral content (BMC) is lower than normal.

Both conditions are frequent in preterm and/or low birth weight infants and/or infants suffering from suboptimal intra-uterine nutrition and lead to an increased risk of bone fractures in these populations (Arch Dis Child Fetal Neonatal Ed 2002 86: F82-F85). Infants, children and adolescents suffering from growth retardation due to malnutrition and/or disease are also frequently affected by these conditions.

Osteomalacia in children is usually associated to rickets, whereas osteopenia is often restricted to the wilder, adult form of the disease. Osteomalacia is often considered by many doctors to be a precursor to osteoporosis.

Osteoporosis ("porous bones", from Greek) is a disease of bone that leads to an increased risk of fracture. This disease is characterized by too little bone formation, excessive bone loss, or a combination of both. In osteoporosis the bone mineral density (BMD) is reduced, bone microarchitecture is deteriorating, and the amount and variety of proteins in bone is altered.

Osteoporosis is defined by the World Health Organization (WHO) as a bone mineral density (BMD) that is 2.5 standard deviations or more below the mean peak bone mass (average of young, healthy adults) as measured by DXA (Dual-energy X-ray absorptiometry). As a comparison, osteopenia is defined as a bone mineral density between that is between 1.0 and 2.5 standard deviations below said mean peak bone mass. BMD tests provide individuals with a measurement called a T-score, a number value that results from comparing the bone density of the individuals to optimal bone density.

Osteomalacia is a generalized bone condition in which there is inadequate mineralization of the bone. Osteomalacia or rickets may show signs as diffuse body pains, muscle weakness, and fragility of the bones. The most common cause of the disease is a deficiency in vitamin D, which is normally obtained from the diet and a sunlight exposure.

However there is still a need for a nutritional composition for the prevention and/or treatment of bone disease, among which osteopenia, osteomalacia, rickets and osteoporosis, in particular in infants and young children who were born preterm or with low-birth weight (LBW) or experienced intra-uterine growth retardation (IUGR) or who suffered from growth stunting typically because of malnutrition (usually by experiencing suboptimal intra-uterine nutrition) or experienced disease such as Crohn's disease and/or celiac disease and/or cancer or who were treated with drugs leading to malabsorption, anorexia and/or metabolic bone disease, such as chemotherapy drugs and/or corticosteroids.

There is a need for an improvement of bone disease, such as osteopenia, osteomalacia, rickets or osteoporosis, by a non-drug-based intervention that is compatible with fragile individuals like infants or children.

There is a need for a long term effect in the reduction of the frequency, occurrence, severity and/or duration of bone disease. There is furthermore a need for an effect that becomes measurable "later in life", especially some years after the intervention.

There is a need for a nutritional intervention in young mammals, in particular infants and children, but also young pets, who were born preterm or with LBW or experienced IUGR or who suffered from growth stunting because of malnutrition or experienced disease such as Crohn's disease and/or celiac disease and/or cancer or who were treated with drugs leading to malabsorption, anorexia and/or metabolic bone disease, such as chemotherapy drugs and/or corticosteroids.

There is a need for such intervention that induces the maintenance or the improvement of bone health in humans and in animals, especially in young mammals.

SUMMARY OF THE INVENTION

The present inventors have found surprisingly that the administration of a mixture of specific oligosaccharides in combination with at least one long chain polyunsaturated fatty acid (LC-PUFA) and at least one probiotic, is particularly effective in the promotion of healthy bone growth and in the prevention and/or treatment bone disease, in particular osteomalacia, rickets, osteopenia and osteoporosis.

Accordingly, the present invention provides a composition comprising at least one LC-PUFA, at least one probiotic and a mixture of oligosaccharides, said mixture containing at least one N-acetylated oligosaccharide, at least one sialylated oligosaccharide and at least one neutral oligosaccharide, for use in the prevention and/or treatment of bone disease, preferably osteomalacia, rickets, osteopenia or osteoporosis.

The composition according to the invention is preferably a nutritional composition.

The LC-PUFA is preferably chosen among arachidonic acid (ARA) and docosahexanoic acid (DHA), more preferably the LC-PUFA is a mixture of ARA and DHA.

The probiotic is preferably chosen among probiotic bacterial strains, more preferably the probiotic is a *lactobacillus* or a *bifidobacterium*. In a preferred embodiment, the probiotic is *Lactobacillus rhamnosus*, term which covers *Lactobacillus rhamnosus* ATCC 53103 and *Lactobacillus rhamnosus* CGMCC 1.3724 (nick name NCC4007 and LPR), *Lactobacillus reuteri* and *Bifidobacterium lactis*.

The neutral oligosaccharide is preferably chosen among fructooligosaccharides (FOS) and galactooligosaccharides (GOS), preferably GOS.

In one embodiment the oligosaccharide mixture may be derived from animal milk, such as one or more of cow, goat, sheep or buffalo milk. For example, it was obtained by cow's milk fractionation and further enzymatic treatment.

In a second embodiment the oligosaccharide mixture may be prepared using enzymatic, chemo-enzymatic and/or chemical means.

In a third embodiment the oligosaccharide mixture may be prepared using yeast and/or bacterial fermentation technologies. For example, yeast and/or bacterial cells expressing suitable enzymes such as glycosidases and/or glycosyltransferases upon genetic modification or not, might be used to this end.

The invention comprises three different types of uses of the composition according to the invention. In the first case, individuals and particularly children are healthy, without any risk of bone disease because of no history of bone disease in their family. In the second case, individuals and particularly children are healthy, but at risk of bone disease because of history of bone disease in their family or because they were born preterm or with LBW or experienced IUGR or who suffered periods of growth stunting or experienced disease such as Crohn's disease and/or celiac disease and/or cancer or who were treated with drugs leading to malabsorption, anorexia and/or metabolic bone disease, such as chemotherapy drugs and/or corticosteroids In the third case, individuals and particularly children have a bone disease, and hence are sick. The preferred use according to the invention is the second case, for preterm/LBW/IUGR infants and also for infant/children suffering from growth delays because of disease or malnutrition or drugs' use.

DETAILED DESCRIPTION OF THE INVENTION

As used herein, the following terms have the following meanings.

The term "child" means a human between the stages of birth and puberty. An adult is a human older than a child.

The term "infant" means a child under the age of 12 months.

The term "preterm infant" means an infant born at least than 37 weeks gestational age.

The term "low birth weight infant" means an infant having a liveborn weight less than 2,500 g.

The term "young child" means a child aged between one and three years.

The term "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The term "preterm infant formula" means an infant formula intended for a preterm infant.

The term "human milk fortifier" means a supplement used to increase the calories, protein, minerals and vitamins in breast milk fed to preterm infants or infants with a low birth weight.

The term "follow-on formula" means a foodstuff intended for particular nutritional use by infants aged over four months and constituting the principal liquid element in the progressively diversified diet of this category of person.

The term "starter infant formula" means a foodstuff intended for particular nutritional use by infants during the first four months of life.

The term "baby food" means a foodstuff intended for particular nutritional use by infants during the first years of life.

The term "infant cereal composition" means a foodstuff intended for particular nutritional use by infants during the first years of life.

The term "growing-up milk" means a milk-based beverage adapted for the specific nutritional needs of young children.

The term "weaning period" means the period during which the mother's milk or the infant formula is partially or totally substituted by other food in the diet of an infant.

The term "bone disease" refers to the medical conditions which affect the bone, in particular related to the reduction of bone organic matrix, such as osteopenia or osteoporosis and/or to a reduction in bone mineralization, such as osteomalacia and rickets.

The term "prevention and/or treatment of bone disease" means the prevention and the reduction of frequency and/or occurrence and/or severity and/or duration of bone disease. Occurrence is related to the number of any bone disease. Frequency is related to the number of the same bone disease. This prevention encompasses the reduction of frequency and/or of severity of said bone disease later in life. The term "later in life" encompasses the effect after the termination of the intervention. The effect "later in life" can be preferably 2 to 4 weeks, 2 to 12 months or years (e.g. 2, 5, 10 years) after the termination of said intervention. A fracture can be a consequence of a bone disease such as the above.

The term "promotion of healthy bone growth" means the support of the bone growth so it is accomplished in the most balanced way.

The term "nutritional composition" means a composition which nourishes a subject. This nutritional composition is usually to be taken orally, intragastrically, or intravenously, and it usually includes a lipid or fat source and a protein source.

The term "synthetic mixture" means a mixture obtained by chemical and/or biological means, which can be chemically identical to the mixture naturally occurring in mammalian milks.

The term "hypoallergenic composition" means a composition which is unlikely to cause allergic reactions.

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999: 10 107-10).

The term "oligosaccharide" means a carbohydrate having a degree of polymerisation (DP) ranging from 2 to 20 inclusive but not including lactose.

The term "neutral oligosaccharide" means an oligosaccharide having no charge and no N-acetyl residue.

The term "sialylated oligosaccharide" means an oligosaccharide having a sialic acid (such as N-acetylneuraminic acid and/or N-glycolylneuraminic acid) residue.

The term "N-acetylated" oligosaccharide means an oligosaccharide having at least one hexose carrying an N-acetyl residue.

NCC designates Nestlé Culture Collection.

All percentages are by weight unless otherwise stated.

In one aspect, the invention provides a composition, comprising
 at least one LC-PUFA,
 at least one probiotic, and
 a oligosaccharide mixture, said mixture containing at least
  one N-acetylated oligosaccharide selected from the group comprising GalNAcα1,3Galββ1,4Glc (=3'Gal-NAc-lac=N-acetyl-galactosaminyl-lactose), Galββ1,6GalNAcα1,3Galβ1,4Glc (=6'Gal-3GalNAc-lac=galactosyl-N-acetyl-galactosaminyl-lactose), Galβ1,4GlcNAcβ1,3Galβ1,4Glc (lacto-N-neotetraose or LNnT) and Galβ1,3GlcNAcβ1,3Galβ1,4Glc (lacto-N-tetraose or LNT), at least one sialylated oligosaccharide selected from the group comprising NeuAcα2,3Galβ1,4Glc (=3'-sialyllactose) and NeuAcα2,6Galβ1,4Glc (=6'-sialyllactose), and at least one neutral oligosaccharide selected form the group consisting of Galβ1,6Gal (=β1,6-digalactoside); Galβ1,6Galβ1,4Glc (=6' Gal-lac); Galβ1,6Galβ1,6Glc; Galβ1,3Galβ1,3Glc; Galβ1,3Galβ1,4Glc (=3'Gal-lac); Galβ1,6Galβ1,6Galβ1,4Glc (=6',6-diGal-lac); Galβ1,6Galβ1,3Galβ1,4Glc (=6',3-diGal-lac); Galβ1,3Galβ1,6Galβ1,4Glc (=3',6-diGal-lac); Galβ1,3Galβ1,3Galβ1,4Glc (=3',3-diGal-lac); Galβ1,4Galβ1,4Glc (=4' Gal-lac) and Galβ1,4Galβ1,4Galβ1,4Glc (=4',4-diGal-lac); and Fucα1,2Galβ1,4Glc (=2' fucosyllactose or FL), for use in the promotion of healthy bone growth and in the prevention and/or treatment of bone disease, preferably osteomalacia, rickets, osteopenia or osteoporosis.

In a second aspect, the invention relates to a composition comprising at least one long chain polyunsaturated fatty acid, at least one probiotic, and an oligosaccharide mixture which comprises:

0.25-20 wt %, preferably 0.3-10 wt %, more preferably 0.3-5 wt % and even more preferably around 0.5 wt %, with respect to the total weight of the oligosaccharide mixture, of at least one N-acetylated oligosaccharide, 0.5-30 wt %, preferably 0.75-15 wt %, more preferably 0.75-10 wt % and even more preferably around 1 wt %, with respect to the total weight of the oligosaccharide mixture, of at least one sialylated oligosaccharide, and 50-99.3 wt %, preferably 20-80 wt %, more preferably 10-50 wt % and even more preferably around 50 wt %, with respect to the total weight of the oligosaccharide mixture, of at least one neutral oligosaccharide, for use in the promotion of healthy bone growth and in the prevention and/or treatment of bone disease, preferably osteomalacia, rickets, osteopenia or osteoporosis.

According to a preferred embodiment, the oligosaccharide mixture is present in an amount of 0.5-70%, more preferably 1-20%, even more preferably 2-5%, with respect to the total weight of the composition.

The oligosaccharide compounds are defined by their structures, where GalNAc is N-acetyl galactosamine, GlcNAc is N-acetyl glucosamine, Gal is galactose, NeuAc is N-acetyl neuraminic acid, Glc is glucose and Fuc is fucose.

The oligosaccharide mixture of the composition according to the invention is preferably the only source of oligosaccharide in said composition.

In a first embodiment, the neutral oligosaccharide is preferably chosen among FOS and GOS, preferably GOS such as the ones cited above.

In a second embodiment, independent or not from the first embodiment, the neutral oligosaccharide is preferably 2'-fucosyllactose (FL). In this case, FL is preferably included in the group of neutral oligosaccharides in the oligosaccharide mixture during its manufacturing. The neutral oligosaccharide may be prepared as a mixture by purchasing and mixing the individual components. For example, synthesised galacto-oligosaccharides such as Galβ1,6Gal, Galβ1,6Galβ1,4Glc, Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc and mixtures thereof are commercially available under the trademarks Vivinal® from Friesland Campina, Netherlands, and Elix'or®. Other suppliers of oligosaccharides are Dextra Laboratories, Sigma-Aldrich Chemie GmbH and Kyowa Hakko Kogyo Co., Ltd. Alternatively, specific glycosyltransferases and/or glycosidases, such as galactosyltransferases and/or fucosyltransferases and/or galactosidases and/or fucosidases, may be used to produce galacto-oligosaccharides and/or fucosylated oligosaccharides.

The fucosyllactose is a fucosylated oligosaccharide (that is to say an oligosaccharide having a fucose residue). This fucosylated oligosaccharide may be isolated by chromatography or filtration technology from a natural source such as animal milks. Alternatively, it may be produced by biotechnological means using specific fucosyltransferases and/or fucosidase either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used.

Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

According to the invention, the sialylated oligosaccharide can be selected from the group comprising 3'-sialyllactose and 6'-sialyllactose. Preferably, the sialylated oligosaccharide comprises both 3'-sialyllactose and 6'-sialyllactose. In this embodiment, the ratio between 3'-sialyllactose and 6'-sialyllactose lies preferably in the range between 5:1 and 1:2.

The 3'- and 6'- forms of sialyllactose may be obtained by adding to the composition a natural source such as animal milk, or may be isolated by chromatographic or filtration technology from such natural source. Alternatively, they may be produced by biotechnological means using specific sialyltransferases or sialidases, neuraminidases, by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

The N-acetylated oligosaccharides may be obtained by adding to the composition a natural source such as animal milk. Alternatively, they may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced through the use of fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP), from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

LNnT and LNT may be synthesised by enzymatic transfer of saccharide units from donor moieties to acceptor moieties using glycosylhydrolases and/or glycosyltransferases as described for example in U.S. Pat. No. 5,288,637 and WO 96/10086. Alternatively, LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

Preferably the N-acetylated oligosaccharide is selected from the group comprising lacto-N-neotetraose (or LNnT) and lacto-N-tetraose (or LNT). Preferably LNnT and/or LNT are included in the group of sialylated oligosaccharides in the oligosaccharide mixture during its manufacturing.

Probiotic bacterial strain present in the composition of the invention may be selected from any strain which satisfies the definition of a probiotic and has acceptable shelf-life for the composition in which it will be incorporated. For example, if the composition is incorporated into an infant formulae, said infant formulae is required to remain stable and effective for up to 12 months.

The probiotic bacterial strain is preferably a *lactobacillus* or a *bifidobacterium*. Examples of preferred *Lactobacillus* species are *Lactobacillus rhamnosus*, *Lactobacillus paracasei* and *Lactobacillus reuteri*. Particularly preferred strains are *Lactobacillus rhamnosus* ATCC 53103, *Lactobacillus rhamnosus* CGMCC 1.3724, and *Lactobacillus paracasei* CNCM I-2116. Even more preferably the probiotic is *Lactobacillus Rhamnosus*, term which covers *Lactobacillus Rhamnosus* ATCC 53103 and *Lactobacillus Rhamnosus* CGMCC 1.3724.

*Lactobacillus rhamnosus* ATCC 53103 is available from Valio Oy of Finland under the trademark LGG.

Examples of preferred *Bifidobacterium* species include *Bifidobacterium lactis*, *Bifidobacterium longum*, *Bifidobacterium breve* and *Bifidobacterium infantis*, Particularly preferred strains are *Bifidobacterium lactis* CNCM I-3446 sold inter alia by the Christian Hansen company of Denmark under the trade mark Bb12, *Bifidobacterium longum* ATCC BAA-999 sold by Morinaga Milk Industry Co. Ltd. of Japan under the trade mark BB536, the strain of *Bifidobacterium breve* sold by Danisco under the trade mark Bb-03, the strain of *Bifidobacterium breve* sold by Morinaga under the trade mark M-16V, the strain of *Bifidobacterium infantis* sold by Procter & Gamble Co. under the trade mark Bifantis and the strain of *Bifidobacterium breve* sold by Institut Rosell (Lallemand) under the trade mark R0070.

According to an embodiment of the invention, the probiotic is chosen among probiotic bacterial strains, preferably the probiotic is a *lactobacillus* or a *bifidobacterium*, more preferably the probiotic is *Lactobacillus rhamnosus*, *Lactobacillus reuteri* and *Bifidobacterium lactis*.

The probiotic can be present in the composition in a wide range of percentages provided that the probiotic delivers the effect described. However, preferably, the probiotic is present in the composition in an amount equivalent to from 10e2 to 10e12 cfu (=colony forming unit) of probiotic bacterial strain, more preferably between 10e6 and 10e9 cfu, for each gram of the composition. This expression includes the possibilities that the bacteria are alive, inactivated or dead or even present as fragments such as DNA, cell wall materials, intracellular materials or bacteria metabolites. In other words, the quantity of bacteria which the composition contains is expressed in terms of colony forming ability of that quantity of bacteria if all the bacteria were live irrespective of whether they are, in fact, live, inactivated or dead, fragmented or a mixture of any or all of these states.

The composition contains at least one LC-PUFA, which is usually a n-3 or a n6 LC-PUFA. The n-3 LC-PUFA can be a C20 or a C22 n-3 fatty acid. The C20 or C22 n-3 LC-PUFA is preferably present in an amount of at least 0.1 wt % of all fatty acids in the composition. Preferably the n-3 LC-PUFA is docosahexanoic acid (DHA, C22:6, n-3). The n-6 LC-PUFA can be a C20 or a C22 n-6 fatty acid. The C20 or C22 n-6 LC-PUFA is preferably present in an amount of at least 0.1 wt % of all fatty acids in the composition. Preferably the n-6 LC-PUFA is arachidonic acid (ARA, C20:4, n-6). The source of LC-PUFA may be, for example, egg lipids, fungal oil, low EPA fish oil or algal oil. The LC-PUFA of the composition of the invention may be provided in small amounts of oils containing high quantities of preformed arachidonic acid and docosahexanoic acid such as fish oils or microbial oils.

The composition according to the invention is preferably a nutritional composition, more preferably a synthetic nutritional composition. In this case, it can be a preterm infant formula, a human milk fortifier, a starter infant formula, a follow-on formula, a baby food formula, an infant cereal formula, a growing-up milk, a medical food product for clinical nutrition, or a supplement, typically to be used during hospital stay and/or to be used after hospital discharge. A supplement can be for a preterm infant or a child or an adult. Said composition is preferably a product for preterm feeding such as a preterm infant formula, a human milk fortifier, or a preterm infant supplement. According to an embodiment, the composition is preferably a preterm infant formula, a human milk fortifier, or a supplement. The composition according to the invention can also be products for children or adults such as yogurt or medical food, as well as pets' food.

According to a particularly preferred embodiment, the composition according to the invention is for use in infants and young children who were born preterm or with LBW or experienced IUGR, preferably in infants who experienced IUGR, or who suffered from growth stunting, typically because of malnutrition or experienced disease such as Crohn's disease and/or celiac disease and/or cancer or who were treated with drugs leading to malabsorption, anorexia and/or metabolic bone disease, such as chemotherapy drugs and/or corticosteroids.

The composition according to the invention can be for use before and/or during and/or after a weaning period.

Preferably the composition according to the invention is for use in the promotion of healthy bone growth and/or in the prevention and the reduction of frequency and/or occurrence and/or severity and/or duration of bone disease.

Particularly the composition according to the invention is for use in the prevention and the reduction of frequency and/or occurrence and/or severity and/or duration of fractures.

Preferably the composition according to the invention is for use in the promotion of healthy bone growth. More preferably, the composition according to the invention is for use in the prevention of reduction of BMD and/or for use in the enhancement of bone mineral content (BMC).

The invention includes also the use of a composition according to the invention, as a synthetic nutritional agent, for the promotion of healthy bone growth and/or for the prevention and/or treatment of bone disease, particularly osteomalacia, rickets, osteopenia or osteoporosis.

The invention includes also the use of a composition according to the invention, as a synthetic nutritional agent, for the prevention of reduction of BMD and/or the enhancement of BMC.

These uses encompass the case where the composition is a supplement, preferably provided in the form of unit doses.

All the uses stated above are particularly intended for infants and young children. The compositions and uses as per the present invention are particularly suited for infants and young children at risk of bone disease, having a family history of bone disease, or having already experienced at least one, preferably several, episode(s) of fracture. The compositions and uses as per the present invention are particularly suited for infants and young children who were born preterm or with LBW or experienced IUGR or who suffered from growth stunting because of malnutrition or experienced disease such as Crohn's disease and/or celiac disease and/or cancer or who were treated with drugs leading to malabsorption, anorexia and/or metabolic bone disease, such as chemotherapy drugs and/or corticosteroids. The composition of the invention can also apply to teenagers or adults at risk of bone disease or having experienced at least one, preferably several, episode(s) of fractures, or who were born preterm or with LBW or experienced IUGR of who suffered from growth stunting because of malnutrition or experienced disease such as Crohn's disease and/or celiac disease and/or cancer or who were treated with drugs leading to malabsorption, anorexia and/or metabolic bone disease, such as chemotherapy drugs and/or corticosteroids or who suffered from growth delays because of disease or malnutrition or drugs' use during infancy and/or childhood (including adolescence).

The composition according to the invention is particularly preferred for use in infants and children who were born preterm or with low-birth weight or experienced intra-uterine growth retardation, or with intra-uterine malnutrition or who suffered growth delay.

Without wishing to be bound by theory, the inventors believe that the efficacy of the combination of oligosaccharide mixture in the composition described above in the promotion of healthy bone growth and/or in the prevention and/or treatment of bone disease, may be the result of the synergistic combination of immunity modulator effects triggered by the probiotic bacterial strain and the LC-PUFA through their stimulation with the specific oligosaccharide mixture.

The oligosaccharides, the LC-PUFA and the probiotic bacterial strain may be administered in the same composition or may be administered sequentially.

If the preterm and LBW infant group is to be addressed, the composition is preferably a nutritional composition, for example consumed in liquid form. It may be a nutritionally complete formula such as a (preterm) infant formula, a supplement, a human milk fortifier, a follow-on formula or a growing-up milk. Alternatively for the group of young children, the composition may be a juice drink or other chilled or shelf stable beverage or a soup, for example, or a baby food, or an infant cereal composition. Alternatively, for the group of young mammals, the composition may be a pets' food.

The composition according to the invention can also contain a protein source. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions. The proteins can be at last partially hydrolysed in order to enhancement of oral tolerance to allergens, especially food allergens. In that case the composition is a hypoallergenic composition.

The composition according to the present invention can also contain a carbohydrate source in addition to the oligosaccharide mixture. This is particularly preferable in the case where the composition of the invention is an infant formula. In this case, any carbohydrate source conventionally found in infant formulae such as lactose, saccharose, maltodextrin, starch and mixtures thereof may be used although the preferred source of carbohydrates is lactose. In any case, the oligosaccharide mixture is preferably the single source of prebiotic in the composition according to the invention.

The composition according to the present invention can also contain a source of lipids in addition to the LC-PUFA. This is particularly relevant if the nutritional composition of the invention is an infant formula. In this case, the lipid source may be any lipid or fat which is suitable for use in infant formulae. Preferred fat sources include palm oleic, high oleic sunflower oil and high oleic safflower oil. The essential fatty acids linoleic and α-linolenic acid may also be added. In the composition, the fat source (including the LC-PUFA such as ARA and/or DHA) preferably has a ratio of n-6 to n-3 fatty acids of about 1:2 to about 10:1, preferably about 3:1 to about 8:1.

The composition of the invention can also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the composition of the invention may contain emulsifiers and stabilisers such as soy, lecithin, citric acid esters of mono- and di-glycerides, and the like.

The composition of the invention may also contain other substances which may have a beneficial effect such as lactoferrin, nucleotides, nucleosides, gangliosides, polyamines, and the like.

The preparation of the composition according to the invention will now be described by way of example.

The formula may be prepared in any suitable manner. For example, it may be prepared by blending together a protein source, a carbohydrate source (different from the oligosaccharide mixture), and a fat source including the LC-PUFA in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The oligosaccharide mixture will be added at this stage if the final product is to have a liquid form. If the final product is to be a powder, the oligosaccharides may likewise be added at this stage if desired. The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

The homogenised mixture is transferred to a suitable drying apparatus such as a spray dryer or freeze dryer and converted to powder. The powder should have a moisture content of less than about 5% by weight. The oligosaccharide mixture may be added at this stage by dry-mixing along with the probiotic bacterial strain(s), or by blending them in a syrup form of crystals, along with the probiotic bacterial strain(s), and spray-dry (or freeze-dry).

If a liquid composition is preferred, the homogenised mixture may be sterilised then aseptically filled into suitable containers or may be first filled into the containers and then retorted.

In another embodiment, the composition of the invention may be a supplement in an amount sufficient to achieve the desired effect in an individual. This form of administration is more suited to preterm or LBW or IUGR infants, older children and adults.

The amount of oligosaccharide mixture, LC-PUFA and probiotic bacterial strain to be included in the supplement will be selected according to the manner in which the supplement is to be administered.

The supplement may be in the form of powder, tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

The supplement can be added in a product acceptable to the consumer (who is a human or an animal), such as an ingestible carrier or support, respectively. Examples of such carriers or supports are a pharmaceutical or a food or a pet food composition. Non-limiting examples for such compositions are milk, yogurt, curd, cheese, fermented milks, milk based fermented products, fermented cereal based products, milk based powders, human milk, preterm formula, infant formula, oral supplement, and tube feeding.

Further, the supplement may contain an organic or inorganic carrier material suitable for enteral or parenteral administration as well as vitamins, minerals trace elements and other micronutrients in accordance with the recommendations of Government bodies such as the USRDA.

The advantages, nature, and various additional features of the invention will appear more fully upon consideration of the illustrative experiment now to be described in detail in connection with accompanying drawings. In the drawings.

EXAMPLE

Experiments were carried out with respect to the effect of the supplementation of a oligosaccharide mixture which is a mixture of cow milk oligosaccharides (CMOS) enriched with galacto-oligosaccharides (demineralized, delactosed whey permeate or DDWP), LC-PUFA (arachidonic acid—ARA—and docosahexaenoic acid—DHA—), and *Lactobacillus rhamnosus*, on rats who experienced IUGR. IUGR was induced by 50% maternal food restriction from day 11 of gestation to delivery.

1. Methodology

Sprague-Dawley timely mated females and non mated females were purchased from Charles River, France. Mated females were blocked by weight and allocated to ad libitum or restricted regimen. All animals received a chow diet (Kliba 3437). Restricted females received 50% intake of the non-mated females from day 11 of gestation until delivery, after which all females were allowed to feed ad libitum.

At birth, pups were weighed within the first 24 hrs and allocated to one of three groups (12 males and 12 females each):
  a) Control: Pups from ad libitum fed dams receiving control gavage and control weaning diet;
  b) IUGR control (IUGRc): Pups from restricted mothers receiving control gavage and control weaning diet;
  c) IUGR mixture (IUGRtx): Pups from restricted mothers receiving treatment gavage and treatment weaning diet.

In order to minimize maternal effects, pups in the study were randomly selected from each of the mothers and allocated to 4 nursing dams per group, thus, siblings from the same litter were randomly allocated into the two IUGR groups. Control pups were nursed by dams fed ad libitum during gestation and pups in IUGR groups by dams restricted during gestation.

Litters were adjusted to 8 pups each (4 males and 4 females), from which 6 from each litter (3 males and 3 females) were included in the experimental groups. Pups remained with their assigned dams and were allowed to suckle ad libitum until 21 days of age.

2. Treatment and Diets

The following functional ingredients were used for experimental gavage and diet composition:

a) DDWP ingredient at 98.8% dry matter, which composition is detailed in Table 1.

TABLE 1

Composition of DDWP mixture

| | % of Dry matter |
|---|---|
| Lactose | 33.4 |
| Total oligosaccharides | 25.51 |
| Glucose | 9.06 |
| Galactose | 8.13 |
| Protein | 4.03 |
| Ash | 11.43 |
| Unknown | 8.44 |

The DDWP is typically obtained according to the disclosures of WO2007/101675 or WO 2007/090894 and usually contains a mixture of about 30 wt % of GalNAc$\alpha$1,3Gal$\beta$1,4Glc and Gal$\beta$1,6GalNAc$\alpha$1,3Gal$\beta$1,4Glc; 50 wt % of Gal$\beta$1,6Gal$\beta$1,4Glc and Gal$\beta$1,3Gal$\beta$1,4Glc; 20 wt % of NeuAc$\alpha$2,3Gal$\beta$1,4Glc and NeuAc$\alpha$2,6Gal$\beta$1,4Glc.

b) NCC 4007 (*Lactobacillus rhamnosus*) freeze dried culture powder with skim milk containing $2.14 \times 10^{11}$ cfu per gram.

c) ARASCO® oil containing 43.6% arachidonic acid (ARA) and DHASCO® oil containing 43.6% of docosahexanoic acid (DHA) (Martek Biosciences Corporation).

2.1. Gavage

From 7 to 21 d pups received either control or treatment gavage. The treatment gavage aimed to provide DDWP at 0.08% of body weight (BW), DHA and ARA at 0.03% of BW and $1 \times 10^9$ CFU of NCC 4007 per day. In the placebo gavage DDWP was substituted by maltodextrin (Glucidex 12, Roquette), DHA and ARA were substituted by $\alpha$-linolenic acid (C18:3 n-3) and linoleic acid (C18:2 n-6) respectively, and freeze dried NCC 4007 was replaced by skim milk powder. Other carbohydrates present in the DDWP mixture (see Table 1) were also provided in the placebo gavage.

2.2. Diets

At day 21, pups were individually housed and weaned to either control (Control and IUGRc) or experimental diet (IUGRtx) which they received until day (=post natal day) 58. Weaning diets (Tables 2 and 3) were in powder form and were stored at 4° C. in vacuum sealed aluminium packs until use.

TABLE 2

Composition of weaning diets (g/100 g of diet)

| | Control[1] | Treatment[2] |
|---|---|---|
| K-caseinate[3] | 20 | 20 |
| Corn starch[4] | 33.95 | 33.95 |
| Maltodextrin[5] | 16.79 | 9.58 |
| Sucrose[6] | 10 | 10 |
| Lactose[7] | 4.76 | 0 |
| Glucose[8] | 1.29 | 0 |
| Galactose[7] | 1.16 | 0 |
| DDWP mixture[9] | 0 | 14.42 |
| Fat mix (see below table 3 for composition) | 7 | 7 |
| Minerals (AIN-93-G)[10] | 3.50 | 3.50 |
| Vitamins (AIN-93-VX)[10] | 1 | 1 |
| L-Cysteine[7] | 0.30 | 0.30 |
| Choline bitartrate[4] | 0.25 | 0.25 |

[1]4.53 kcal/g, 18.32% protein
[2]4.46 kcal/g, 18.78% protein
[3]Smith trading Co.
[4]Synopharm, Germany,
[5]Roquette, France.
[6]Howeg, Switzerland.
[7]Fluka,
[8]Merck, Germany.
[9]Nestlé, Switzerland,
[10]Socochim, Switzerland.

TABLE 3

Fat mix (g/100 g of fat)

| | | |
|---|---|---|
| Refined Palm Olein[11] | 50 | 54 |
| Coconut oil[11] | 15 | 11 |
| Low erucic rapeseed oil[11] | 15 | 12 |
| Corn oil[12] | 14 | 10 |
| ARASCO[13] | 0 | 5 |
| DHASCO[13] | 0 | 5 |
| Flaxseed oil[15] | 6 | 3 |

[11]Sofinol, Switzerland.
[12]Nutriswiss, Switzerland.
[13]Martek, USA.
[14]Sabo, Switzerland In the experiments, the ratios are as follows: Gavage: DDWP:ARA:DHA 1:1:1 and Diet: DDWP:ARA:DHA 11:1:1

The nutritional content of both diets (modified AIN 93 G) was adapted to the rat requirements for growth. Control diet was supplemented with lactose, glucose, galactose to match the levels of these carbohydrates found in the DDWP product.

The fatty acid profile of the two diets was balanced to provide similar ratio of n-6/n-3 and similar proportion of saturated, monounsaturated and polyunsaturated fatty acids.

The fatty acid composition of both diets was nearly the same in terms of fatty acid profile, except for C18:2 n-6 (linoleic acid) which is of 16.8% Mass FA for the control and 14.6 for the treatment, C18:3 n-3 ($\alpha$-linolenic acid) which is of 4.1% Mass FA for the control and 2.5 for the treatment, C20:4 n-9 (ARA) which is 0.0 for the control and 2.1% Mass FA for the treatment and C22:6 n-3 (DHA) which is 0.0 for the control and 1.9% Mass FA for the treatment. The total n-6 for the control and for the treatment is of 18.0% Mass FA. The total n-3 is of 4.1% Mass FA for the control and 4.4% Mass FA for the treatment, which is quite similar, and the n-6/n-3 ratio is of 4.4% Mass FA for the control and 4.1 for the treatment, which is similar.

During this period, animals received a gelatin pellet with (IUGR-treatment) or without (Control and IUGR-control)

NCC 4007 (1×10$^9$ CFU). The pellets were supplemented every morning, and their composition is detailed in Table 4.

TABLE 4

Composition of gelatin pellets

|  | Control | Treatment |
|---|---|---|
| Gelatin (mg) | 45 | 45 |
| DDWP (mg) | 0 | 15 |
| Carbohydrate mix | 15 | 0 |
| NCC 4007 (mg) | 0 | 4.6 |
| Skim milk (mg) | 4.6 | 0 |
| PBS + peptone (microL) | 300 | 300 |
| Saccharine (mg) | 0.2 | 0.2 |

The animals were sacrificed on day 58.

3. Bone Parameters

Before sacrifice, the nose-anus length was measured.

After sacrifice femurs were collected. The bones were defleshed with care in order to leave the periosteum intact. After measuring their length, femurs were stored hydrated in gauze soaked with phosphate-buffered saline at −80° C. Each femur was brought to room temperature before measurement.

Bone mineral content (BMC) and bone mineral (BMD) of the whole femur were determined using dual energy X-ray absorptiometry (DXA). The femur was placed on a reference excised bone plate (purchased by PIXImus) which mimics soft tissue and it was scanned using DXA (PIXImus2; GE-Lunar, Madison, Wis.). The coefficient of variance for total BMD and BMC was 0.5%.

Figure 1:
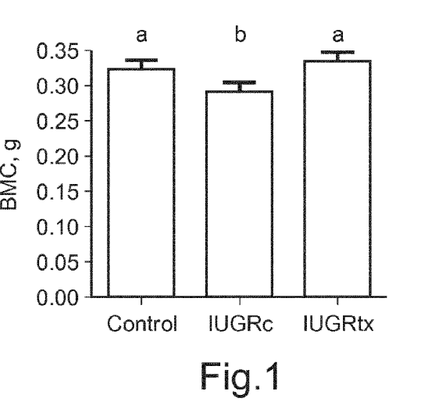
FIG. 1 is a bar graph plotting the results of the experiments, in terms of Bone Mineral Concentration (BMC, in g).

FIG. 1 is a bar graph plotting the results of the experiments, in terms of Bone Mineral Content (BMC, in g), at day (=post natal day) 58.

Figure 2:
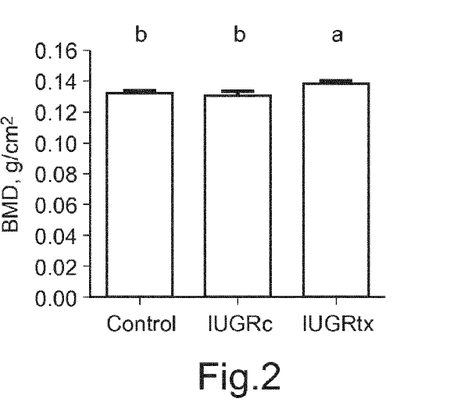
FIG. 2 is a bar graph plotting the results of the experiments, in terms of Bone Mineral Density (BMD, in $g/cm^2$).

FIG. 2 is a bar graph plotting the results of the experiments, in terms of Bone Mineral Density (BMD, in g/cm$^2$), at day (=post natal day) 58. Columns indicate median±SE median of the group. Males and females are plotted together. The "a" and "b" letters have the following meanings: different letters mean significant differences (p<0.005).

Figure 3:
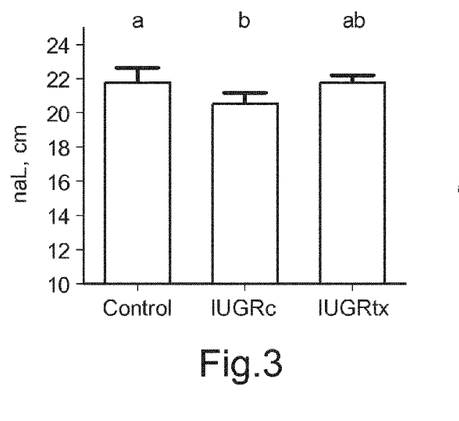
FIG. 3 is a bar graph plotting the results of the experiments, in terms of nose-anus length (or naL in cm).

FIG. 3 is a bar graph plotting the results of the experiments, in terms of nose-anus length (or naL in cm), at day (=post natal day) 58.

Figure 4:
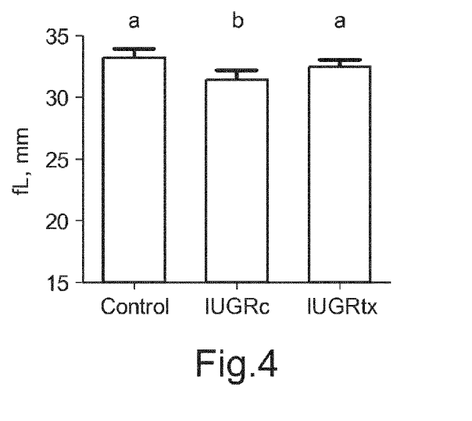
FIG. 4 is a bar graph plotting the results of the experiments, in terms of femur length (or fL in mm).

FIG. 4 is a bar graph plotting the results of the experiments, in terms of femur length (or fL in mm), at day (=post natal day) 58. Columns indicates median±SE median of the groups. Males and females are plotted together. The "a" and "b" letters have the following meanings: different letters mean significant differences (p<0.005).

From those results, it appears that nose-anus length (naL) was decreased in IUGRc compared to Control, whereas there were no differences between Control and IUGRtx (FIG. 3, IUGRc vs. Control, P<0.01 and IUGRtx vs IUGRc, P=0.059). Femur length (fL) was decreased in IUGRc compared to Control and IUGRtx; there were not differences between Control and IUGRtx. (FIG. 4, IUGRc vs. Control IUGRtx, P=0.027). Similarly, the BMC was decreased in IUGRc compared to Control and IUGRtx (FIG. 1, P≤0.003); there were no differences between IUGRtx and Control. BMD was increased by IUGRtx with respect to the Control and IUGRc (FIG. 2, P≤0.003).

The invention claimed is:

1. A method for treatment of osteomalacia, rickets, osteopenia or osteoporosis in an individual in need of same, the method comprising administering to the individual a composition as a synthetic nutritional agent, the composition comprising at least one long chain polyunsaturated fatty acid (LC-PUFA); at least one probiotic; and an oligosaccharide mixture, the oligosaccharide mixture comprising 0.25-20 wt. % with respect to the total weight of the oligosaccharide mixture of at least one N-acetylated oligosaccharide selected from the group consisting of lacto-N-neotetraose (LNnT) and lacto-N-tetraose (LNT), 0.5-30 wt. % with respect to the total weight of the oligosaccharide mixture of at least one sialylated oligosaccharide, and 50-99.3 wt. % with respect to the total weight of the oligosaccharide mixture of at least one neutral oligosaccharide.

2. The method according to claim 1, wherein each of the at least one neutral oligosaccharides is selected from the group consisting of fructooligosaccharides (FOS) and galactooligosaccharides (GOS).

3. The method according to claim 1, wherein:

each of the at least one sialylated oligosaccharides is selected from the group consisting of NeuAcα2,3Galβ1,4Glc (=3'-sialyllactose) and NeuAcα2,6Galβ1,4Glc (=6'-sialyllactose), and each of the at least one neutral oligosaccharides is selected from the group consisting of Galβ1,6Gal (=β1,6-digalactoside); Galβ1,6Galβ1,4Glc (=6'Gal-lac); Galβ1,6Galβ1,6Glc; Galβ1,3Galβ1,3Glc; Galβ1,3Galβ1,4Glc (=3'Gal-lac); Galβ1,6Galβ1,6Galβ1,4Glc (=6',6-diGal-lac); Galβ1,6Galβ1,3Galβ1,4Glc (=6',3-diGal-lac); Galβ1,3Galβ1,6Galβ1,4Glc (=3',6-diGal-lac); Galβ1,3Galβ1,3Galβ1,4Glc (=3',3-diGal-lac); Galβ1,4Galβ1,4Glc (=4'Gal-lac); Galβ1,4Galβ1,4Galβ1,4Glc (=4',4-diGal-lac); and Fucα1,2Galβ1,4Glc (=2' fucosyllactose).

4. The method according to claim 1, wherein the oligosaccharide mixture is present in an amount of 0.5-70% with respect to the total weight of the composition.

5. The method according to claim 1, wherein each of the at least one LC-PUFAs is selected from the group consisting of arachidonic acid (ARA) and docosahexanoic acid (DHA).

6. The method according to claim 1, wherein the at least one probiotic is a probiotic bacterial strain.

7. The method according to claim 1, wherein each of the at least one sialylated oligosaccharide is selected from the group consisting of 3'-sialyllactose and 6'-sialyllactose.

8. The method according to claim 1, wherein the at least one neutral oligosaccharide comprises 2'-fucosyllactose.

9. The method according to claim 1, wherein the composition is selected from the group consisting of a preterm infant formula, a human milk fortifier, a starter infant formula, a follow-on formula, a baby food formula, an infant cereal formula, a growing-up milk, a medical food product for clinical nutrition and a supplement.

10. The method according to claim 1, wherein the individual is selected from the group consisting of infants and children who were born preterm or with low-birth weight or experienced intra-uterine growth retardation; infants and children who suffered from growth stunting because of malnutrition or experienced anorexia and/or Crohn's disease and/or celiac disease and/or cancer; and infants and children who were treated with drugs leading to malabsorption, anorexia and/or metabolic bone disease.

11. The method according to claim 1, wherein the individual is a preterm infant.

12. A method for promoting healthy bone growth and/or enhancing bone mineral content (BMC) in an individual in need of same, the method comprising administering to the individual a composition as a synthetic nutritional agent, the composition comprising at least one long chain polyunsaturated fatty acid (LC-PUFA); at least one probiotic; and an oligosaccharide mixture, the oligosaccharide mixture comprising 0.25-20 wt. % with respect to the total weight of the oligosaccharide mixture of at least one N-acetylated oligosaccharide selected from the group consisting of lacto-N-neotetraose (LNnT) and lacto-N-tetraose (LNT), 0.5-30 wt. % with respect to the total weight of the oligosaccharide mixture of at least one sialylated oligosaccharide, and 50-99.3 wt. % with respect to the total weight of the oligosaccharide mixture of at least one neutral oligosaccharide.

13. The method according to claim 12, wherein the individual is in need of treatment of reduced bone mineral density (BMD) and/or bone mineral content (BMC).

14. The method according to claim 12, wherein the individual is a preterm infant.

15. The method according to claim 12, wherein each of the at least one neutral oligosaccharides is selected from the group consisting of fructooligosaccharides (FOS) and galactooligosaccharides (GOS).

16. The method according to claim 12, wherein:
each of the at least one sialylated oligosaccharides is selected from the group consisting of 3'-sialyllactose and 6'-sialyllactose, and
each of the at least one neutral oligosaccharides is selected from the group consisting of Galβ1,6Gal (β1,6-digalactoside); Galβ1,6Galβ1,4Glc (=6'Gal-lac); Galβ1,6Galβ1,6Glc; Galβ1,3Galβ1,3Glc; Galβ1,3Galβ1,4Glc (=3'Gal-lac); Galβ1,6Galβ1,6Galβ1,4Glc (=6',6-diGal-lac); Galβ1,6Galβ1,3Galβ1,4Glc (=6',3-diGal-lac); Galβ1,3Galβ1,6Galβ1,4Glc (=3',6-diGal-lac); Galβ1,3Galβ1,3Galβ1,4Glc (=3',3-diGal-lac); Galβ1,4Galβ1,4Glc (=4' Gal-lac); Galβ1,4Galβ1,4Galβ1,4Glc (=4',4-diGal-lac); and Fucα1,2Galβ1,4Glc (=2' fucosyllactose).

17. The method according to claim 12, wherein the oligosaccharide mixture is present in an amount of 0.5-70% with respect to the total weight of the composition.

18. The method according to claim 12, wherein each of the at least one LC-PUFAs is selected from the group consisting of arachidonic acid (ARA) and docosahexanoic acid (DHA).

19. The method according to claim 12, wherein the at least one probiotic is a probiotic bacterial strain.

20. The method according to claim 12, wherein each of the at least one sialylated oligosaccharide is selected from the group consisting of 3'-sialyllactose and 6'-sialyllactose.

21. The method according to claim 12, wherein the at least one neutral oligosaccharide comprises 2'-fucosyllactose.

22. The method according to claim 12, wherein the composition is selected from the group consisting of a preterm infant formula, a human milk fortifier, a starter infant formula, a follow-on formula, a baby food formula, an infant cereal formula, a growing-up milk, a medical food product for clinical nutrition and a supplement.

23. The method according to claim 12, wherein the individual is selected from the group consisting of infants and children who were born preterm or with low-birth weight or experienced intra-uterine growth retardation; infants and children who suffered from growth stunting because of malnutrition or experienced anorexia and/or Crohn's disease and/or celiac disease and/or cancer; and infants and children who were treated with drugs leading to malabsorption, anorexia and/or metabolic bone disease.

* * * * *